United States Patent
Mohsen et al.

(10) Patent No.: US 10,920,264 B2
(45) Date of Patent: Feb. 16, 2021

(54) ACYL-COA DEHYDROGENASES MICRO/NANO ENZYME ASSAY

(71) Applicant: University of Pittsburgh—Of the Commonwealth System of Higher Education, Pittsburgh, PA (US)

(72) Inventors: Al-Walid A. Mohsen, Gibsonia, PA (US); Gerard Vockley, Pittsburgh, PA (US)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 71 days.

(21) Appl. No.: 15/656,414

(22) Filed: Jul. 21, 2017

(65) Prior Publication Data
US 2018/0023113 A1    Jan. 25, 2018

Related U.S. Application Data (60) Provisional application No. 62/365,547, filed on Jul. 22, 2016.

(51) Int. Cl.
*C12Q 1/32* (2006.01)
*G01N 21/64* (2006.01)

(52) U.S. Cl.
CPC ........ *C12Q 1/32* (2013.01); *C12Y 103/99003* (2013.01); *G01N 21/6428* (2013.01); *G01N 2800/04* (2013.01)

(58) Field of Classification Search
CPC ... G01N 21/6428; G01N 21/6452; C12Q 1/32
See application file for complete search history.

(56) References Cited

FOREIGN PATENT DOCUMENTS

WO    WO-2013158616 A1 * 10/2013 ............. A61K 31/06

OTHER PUBLICATIONS

Bertrand et al. Purification of electron transfer flavoprotein from pig liver mitochondria and its application to the diagnosis of deficiencies of acyl-CoA dehydrogenases in human fibroblasts. Clinica Chimica Acta. 1992;210:75-91.*
Broach et al. High-throughput screening for drug discovery. Nature. 1996;384 (Supp 7):14-16.*
Corning. Technical Bulletin #436 Set Up Guidelines and Dimensional Templates for Fluorescence Plate Readers used with Corning® FluoroBlok™ Insert Systems and Corning BioCoat™ Multiwell Insert Cell-Based Assays. Corning. 2004;1-13.*
Lakowicz et al. Quenching of fluorescence by Oxygen. A probe for Structural Fluctuations in Macromolecules. Biochemistry. 1973; 12(21):4161-4170.*
Microplate. Product News: New Microplate Reader Showcased. 2012;1-2.*
Frerman et al., "Fluorometric Assay of Acyl-CoA Dehydrogenases in Normal and Mutant Human Fibroblasts, Biochemical Medicine", 1985, pp. 38-44, vol. 33, Denver, CO.

* cited by examiner

*Primary Examiner* — Lynn Y Fan
(74) *Attorney, Agent, or Firm* — The Webb Law Firm (57) ABSTRACT

Provided herein are methods of measuring acyl-CoA dehydrogenase activity in a biological sample in a multiwell microplate setting.

18 Claims, 2 Drawing Sheets
Specification includes a Sequence Listing.

SEQUENCE LISTING

<160> NUMBER OF SEQ ID NOS: 2

<210> SEQ ID NO 1
<211> LENGTH: 255
<212> TYPE: PRT
<213> ORGANISM: Sus scrofa

<400> SEQUENCE: 1

Met Ala Glu Leu Arg Ala Leu Val Ala Val Lys Arg Val Ile Asp Phe
1               5                   10                  15

Ala Val Lys Ile Arg Val Lys Pro Asp Arg Thr Gly Val Val Met Asp
                20                  25                  30

Gly Val Lys His Ser Met Asn Pro Phe Cys Glu Ile Ala Val Glu Glu
            35                  40                  45

Ala Val Arg Leu Lys Glu Lys Lys Leu Val Lys Glu Val Ile Ala Val
        50                  55                  60

Ser Cys Gly Pro Ala Gln Cys Gln Glu Thr Ile Arg Thr Ala Leu Ala
65                  70                  75                  80

Met Gly Ala Asp Arg Gly Ile His Val Glu Val Pro Ala Ala Glu Ala
                85                  90                  95

His His Leu Gly Pro Leu Gln Val Ala Arg Val Leu Ala Lys Leu Ala
            100                 105                 110

Gln Lys Glu Lys Val Asp Leu Val Leu Leu Gly Lys Gln Ala Ile Asp
        115                 120                 125

```
Asp Asp Cys Asn Gln Thr Gly Gln Met Thr Ala Gly Phe Leu Asp Trp
            130                 135                 140

Pro Gln Gly Thr Phe Ala Ser Gln Val Thr Leu Glu Gly Asp Lys Val
145                 150                 155                 160

Lys Val Glu Arg Glu Ile Asp Gly Gly Leu Glu Thr Leu Arg Leu Lys
                165                 170                 175

Leu Pro Ala Val Val Thr Ala Asp Leu Arg Leu Asn Glu Pro Arg Tyr
            180                 185                 190

Ala Thr Leu Pro Asn Ile Met Lys Ala Lys Lys Lys Ile Glu Val
            195                 200                 205

Ile Lys Ala Gly Asp Leu Gly Val Asp Leu Thr Ser Lys Leu Ser Val
            210                 215                 220

Val Ser Val Glu Asp Pro Pro Gln Arg Val Ala Gly Val Lys Val Glu
225                 230                 235                 240

Thr Thr Glu Asp Leu Val Ala Lys Leu Arg Glu Ile Gly Arg Ile
                245                 250                 255

<210> SEQ ID NO 2
<211> LENGTH: 314
<212> TYPE: PRT
<213> ORGANISM: Sus scrofa

<400> SEQUENCE: 2

Gln Ser Thr Leu Val Ile Ala Glu His Ala Asn Asp Thr Leu Ala Pro
1               5                   10                  15

Ile Thr Leu Asn Thr Ile Thr Ala Ala Lys Arg Leu Gly Gly Glu Val
                20                  25                  30

Ser Cys Leu Val Ala Gly Thr Lys Cys Asp Lys Val Ala Gln Asp Leu
            35                  40                  45

Cys Lys Val Ala Gly Val Ala Lys Val Leu Val Ala Gln His Asp Ala
        50                  55                  60

Tyr Lys Gly Leu Leu Pro Glu Glu Leu Thr Pro Leu Val Leu Ala Thr
65                  70                  75                  80

Gln Lys Gln Phe Asn Tyr Thr His Ile Cys Ala Gly Ala Ser Ala Phe
                85                  90                  95

Gly Lys Asn Leu Leu Pro Arg Ile Ala Ala Lys Leu Asp Val Ala Pro
            100                 105                 110

Ile Ser Asp Ile Ile Ala Ile Lys Ser Pro Asp Thr Phe Val Arg Pro
        115                 120                 125

Ile Tyr Ala Gly Asn Ala Leu Cys Thr Val Lys Cys Asp Glu Lys Val
    130                 135                 140

Lys Val Phe Ser Val Arg Gly Thr Ser Phe Glu Ala Ala Ala Thr Ser
145                 150                 155                 160

Gly Gly Ser Ala Ile Ser Glu Lys Ala Ser Ala Ser Pro Val Gly
                165                 170                 175

Ile Ser Glu Trp Leu Asp Gln Lys Leu Thr Lys Ser Asp Arg Pro Glu
            180                 185                 190

Leu Thr Gly Ala Lys Val Val Val Ser Gly Gly Arg Gly Leu Lys Ser
        195                 200                 205

Gly Glu Asn Phe Lys Leu Leu Tyr Asp Leu Ala Asp Gln Leu His Ala
    210                 215                 220

Ala Val Gly Ala Ser Arg Ala Ala Val Asp Ala Gly Phe Val Pro Asn
225                 230                 235                 240

Asp Met Gln Val Gly Gln Thr Gly Lys Ile Val Ala Pro Glu Leu Tyr
```

-continued

```
                    245                 250                 255
Ile Ala Val Gly Ile Ser Gly Ala Ile Gln His Leu Ala Gly Met Lys
            260                 265                 270

Asp Ser Lys Thr Ile Val Ala Ile Asn Lys Asp Pro Glu Ala Pro Ile
        275                 280                 285

Phe Gln Val Ala Asp Tyr Gly Ile Val Ala Asp Leu Phe Lys Val Val
    290                 295                 300

Pro Glu Met Thr Glu Leu Leu Lys Lys Lys
305                 310
```

ACYL-COA DEHYDROGENASES MICRO/NANO ENZYME ASSAY

CROSS-REFERENCE TO RELATED APPLICATIONS

The present application claims the benefit of U.S. Provisional Patent Application No. 62/365,547, filed Jul. 22, 2016, which is incorporated herein by reference in its entirety.

STATEMENT REGARDING FEDERAL FUNDING

This invention was made with government support under grant numbers HD056004, DK045482, DK054936, and DK078775 awarded by the National Institutes of Health. The government has certain rights in the invention.

REFERENCE TO A SEQUENCING LISTING

The Sequence Listing associated with this application is filed in electronic format via EFS-Web and is hereby incorporated by reference into the specification in its entirety. The name of the text file containing the Sequence Listing is 1705621_ST25.txt. The size of the text file is 5,285 bytes, and the text file was created on Jul. 12, 2017.

BACKGROUND OF THE INVENTION

Field of the Invention

Provided herein are methods of identifying and/or quantifying Acyl-CoA Dehydrogenase activity in a biological sample, and related devices and systems.

Description of the Related Art

The acyl-CoA dehydrogenases (ACDAs) are a family of enzymes that catalyze the $\alpha,\beta$-dehydrogenation of organic acid coenzyme A (CoA) esters. Deficiencies resulting from inborn errors in these enzymes are among the most serious metabolic disorders, as acidic metabolites are life threatening. There are nine members of this family of enzymes that are well characterized. Medium chain acyl-CoA dehydrogenase deficiency (MCADD), very long chain acyl-CoA dehydrogenase deficiency (VLCADD), and isovaleric acidemia (IVA) are the most well characterized deficiencies of this family of enzymes.

Medium-chain acyl-CoA dehydrogenase (MCAD) deficiency and very long-chain acyl-CoA dehydrogenase (VL-CAD) deficiency are conditions that prevents the body from converting certain fats to energy, particularly during periods without food (fasting). Signs and symptoms of MCADD deficiency typically appear during infancy or early childhood and can include vomiting, lack of energy (lethargy), and low blood sugar (hypoglycemia). In rare cases, symptoms of this disorder are not recognized early in life, and the condition is not diagnosed until adulthood. People with MCADD are at risk of serious complications such as seizures, breathing difficulties, liver problems, brain damage, coma, and sudden death. Problems related to MCADD can be triggered by periods of fasting or by illnesses such as viral infections. Signs and symptoms of VLCADD typically appear during infancy or early childhood and can include low blood sugar (hypoglycemia), lack of energy (lethargy), and muscle weakness. Affected individuals are also at risk for serious complications such as liver abnormalities and life-threatening heart problems. When symptoms begin in adolescence or adulthood, they tend to be milder and usually do not involve the heart. Problems related to VLCADD can be triggered by periods of fasting, illness, and exercise. MCADD is related to mutations in the ACADM (medium-chain specific ($C_4$ to $C_{12}$ straight chain) acyl-Coenzyme A dehydrogenase) gene and the estimated incidence of MCADD is 1 in 17,000 people in the U.S. VLCADD is related to mutations in the ACADVL (Acyl-CoA Dehydrogenase, Very Long Chain) gene and is estimated to affect 1 in 40,000 to 120,000 people in the United States.

MCADD is the most frequent inherited defect of fatty acid oxidation and competes with phenylketonuria as the most frequent inborn error of metabolism in humans. MCADD patients are asymptomatic at birth, but are at risk for episodes of acute, life threatening metabolic decompensation. Unless secondary causes accompanied by diminished feeding or fever occur post-delivery, such episodes usually first occur between 3 and 24 months of age, but can occur at any age in association with physiologic stress such as fasting or infection, fever, or strenuous exercise. Prior to acute clinical presentation, physical examination findings may be entirely normal. The mortality rate during an acute crisis in previously undiagnosed patients can be as high as 20%. MCADD can now be identified presymptomatically by newborn screening through mass spectroscopy, nearly eliminating mortality due to this disease, but analysis requires sophisticated MS capabilities at specialized labs, with delayed results especially from rural areas.

Isovaleric acidemia is a rare disorder caused by mutations in the IVD (isovaleryl-CoA dehydrogenase) gene (e.g., GeneCards® GCID: GC15P040405; HGNC:6186; OMIM 607036; UniProtKB P26440; Entrez Gene, Gene ID: 3712), in which the body is unable to process the amino acid leucine. As a result, an organic acid called isovaleric acid and related compounds build up to harmful levels in the body. This buildup damages the brain and nervous system, causing serious health problems. Health problems related to isovaleric acidemia range from very mild to life-threatening. In severe cases, the features of isovaleric acidemia become apparent within a few days after birth. The initial symptoms include poor feeding, vomiting, seizures, and lack of energy (lethargy). These symptoms sometimes progress to more serious medical problems, including seizures, coma, and possibly death. A characteristic sign of isovaleric acidemia is a distinctive odor of sweaty feet during acute illness that is caused by the buildup of isovaleric acid in affected individuals. In other cases, the signs and symptoms of isovaleric acidemia appear during childhood and may come and go over time.

The need exists in the art for a point of care screening test for acyl-CoA dehydrogenase enzymes that is quick and accurate, providing results that could be assessed in minutes rather than days.

SUMMARY

Provided herein are methods of quantifying acyl-coenzyme A dehydrogenase (ACAD) activity in a cell sample. The methods include steps of determining fluorescence of an electron transfer flavoprotein (ETF) in a reaction mixture comprising lysed cells of the cell sample in a well of a multi-well vessel in an anaerobic environment, adding a coenzyme A (CoA) substrate for a specific ACAD to the reaction mixture; and monitoring a change in fluorescence of the ETF at one or more time points after addition of the CoA substrate to the reaction mixture. In the methods, a loss of fluorescence of the ETF indicates the presence of an ACAD in the sample. In some aspects, the cell sample is a human cell sample. In further aspects, the cell sample is free of red blood cells.

In some aspects of the methods disclosed herein, oxygen is removed from the reaction mixture by vacuum. In further aspects, the steps are conducted under an inert gas environment.

In aspects of the methods disclosed herein, the ACAD is a medium-chain specific acyl-CoA dehydrogenase, a very long chain specific acyl-CoA dehydrogenase, an isovaleryl-CoA dehydrogenase, a short-chain specific acyl-CoA dehydrogenase, a long-chain specific acyl-CoA dehydrogenase, an isobutyryl-CoA dehydrogenase, a short/branched-chain acyl-CoA dehydrogenase, an Acyl-CoA Dehydrogenase Family, Member 9, or a glutaryl-CoA dehydrogenase.

In some aspects, the ETF used in the methods disclosed herein is a porcine ETF.

In some aspects of the methods disclosed herein, the reaction mixture in at least one well further comprises a drug that may affect ACAD activity, and wherein a difference in a change in fluorescence of the ETF in the at least one well in which the drug is present compared to one or more wells in which the drug is not present indicates differences in ACAD activity.

In some aspects of the methods disclosed herein, the methods include further steps of adding a drug that may affect ACAD activity to at least one well. In such aspects, a difference in a change in fluorescence of the ETF in the at least one well in which the drug is present compared to one or more wells in which the drug is not present indicates differences in ACAD activity. In other aspects of the methods disclosed herein, lysed cells in a well are contacted with a drug that may affect ACAD activity prior to lysis. In such aspects, a difference in a change in fluorescence of the ETF in the at least one well in which the lysed cells were contacted with the drug prior to lysis compared to one or more wells in which the lysed cells were not contacted with the drug prior to lysis indicates differences in ACAD activity.

Also disclosed herein are methods of quantifying acyl-coenzyme A dehydrogenase (ACAD) activity in a cell sample including steps of adding the cell sample to a well of a multi-well vessel, adding a lysis solution to the well to form a reaction mixture, adding an electron transfer flavoprotein (ETF) to the reaction mixture, removing oxygen from the reaction mixture, determining fluorescence of an electron transfer flavoprotein (ETF) in the reaction mixture, adding a coenzyme A (CoA) substrate for a specific ACAD to the reaction mixture, and monitoring a change in fluorescence of the ETF at one or more time points after addition of the CoA substrate to the reaction mixture. In the methods, a loss of fluorescence of the ETF indicates the presence of an ACAD in the sample.

Also provided herein are methods of quantifying acyl-coenzyme A dehydrogenase (ACAD) activity in a cell sample including the steps of adding the cell sample, comprising at least one ACAD, to a plurality of wells of a multi-well vessel, adding a lysis solution to the plurality of wells to form a reaction mixture, adding an electron transfer flavoprotein (ETF) to the reaction mixture, adding a drug that may affect ACAD activity to at least one, but not all, of the plurality of wells containing the reaction mixture, removing oxygen from the reaction mixture, determining fluorescence of an electron transfer flavoprotein (ETF) in the reaction mixture, adding a coenzyme A (CoA) substrate for the ACAD to the reaction mixture to initiate reaction, and monitoring a change in fluorescence of the ETF at one or more time points after addition of the CoA substrate to the reaction mixture. In the methods, a difference in a change in fluorescence of the ETF in the at least one well in which the drug is present compared to one or more wells in which the drug is not present indicates differences in ACAD activity.

BRIEF DESCRIPTION OF THE DRAWINGS

FIG. 1. Optimizing the ETF fluorescence reduction 96-well plate assay using different detergent concentrations. Samples used were TL596 $4 \times 10^5$ cells with lyses done in wells without lubrol buffer, or with 1/2, 1/5, or 1/10 lubrol, representing 0, 0.5, 0.2, and 0.1% lubrol, respectively. Reaction was initiated after initial baseline fluorescence monitoring for 100 seconds by addition of $C_8$—CoA to 10 µM. The slope reflecting the drop in fluorescence with time was calculated from 100 seconds up to 140 seconds.

DETAILED DESCRIPTION

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases. As used herein "a" and "an" refer to one or more.

Also, it should be understood that any numerical range recited herein is intended to include all sub-ranges subsumed therein. For example, a range of "1 to 10" is intended to include all sub-ranges between and including the recited minimum value of 1 and the recited maximum value of 10, that is, having a minimum value equal to or greater than 1 and a maximum value of equal to or less than 10.

"Patient" or "subject" refers to members of the animal kingdom including but not limited to human beings and "mammal" refers to all mammals, including, but not limited to human beings.

"Comprising," "comprise" or "comprised," and variations thereof, are open ended and do not exclude the presence of other elements not identified. In contrast, the term "consisting of" and variations thereof is intended to be closed, and excludes additional elements in anything but trace amounts.

A "drug," "therapeutic composition" or "active agent" means an active ingredient that is intended to furnish pharmacological activity or other direct effect in the diagnosis, cure, mitigation, treatment, or prevention of disease or to affect the structure or any function of the human body or animal.

An "array" is a structure or combination of structures comprising a plurality of discretely-addressable physical locations. A "multi-well vessel" is a form of array comprising multiple discretely-addressable reaction compartments or chambers. For example, a multi-well vessel can be a 4, 6, 8, 12, 16, 24, 48, or 96 well microplate, or any other plate, cartridge, or other structure containing a plurality of wells.

A "substrate" of an enzyme refers to any substance or composition, such as an amino acid, peptide, polypeptide, molecule, polymer, metabolite, chemical compound, or protein that can be acted on by an enzyme such as an ACAD. A "substrate" as used herein includes tagged, conjugated, or any otherwise modified or derivatized CoA ester compositions that may be acted on by an ACAD.

ACAD assays have been performed in a 1-ml cuvette (Frerman, F. E., et al. Fluorometric Assay of Acyl-CoA Dehydrogenases in Normal and Mutant Human Fibroblasts, *Biochemical Medicine* 33:38-44 (1985)). ACADs can be assessed for activity using a highly sensitive enzyme assay. This assay, known as the electron transfer flavoprotein (ETF) fluorescence reduction assay, relies on detecting a second-half reaction, where the redox partner, ETF, loses its fluorescence upon electron transfer from a substrate-bound ACAD. Prior assays were designed for cuvettes at the 1 ml scale. Typical reaction components for those prior assays include: cell-free extract obtained from patient's fibroblast cells cultured to confluence in a T175 flask, a CoA ester substrate for the specific ACAD enzyme, porcine ETF protein isolated from pig liver, buffer, glucose oxidase, catalase, and glucose. Prior assays also require anaerobic conditions and further require a spectrofluorometer. The design of the assay as such is time- and material-consuming, and would not work for a high volume setting, where immediate results are critical.

An advantage of the micro level assay described herein compared to prior assays is that the assay described herein allows for screening many samples for enzyme activity in a shorter time, with immediate results. Bringing the assay to the micro level essentially as described herein will bring diagnosis to less-sophisticated lab settings.

The assay described herein is useful for a variety of purposes, including, for example and without limitation, screening individual patients for the presence of an ACAD abnormality or deficiency, and screening chemicals for their activity with respect to ACAD function, for example, for screening small molecule chemical libraries to identify chemicals or drugs for their effect on an ACAD phenotype, or to measure other ACAD activity as a reference control for studying fatty acid β-oxidation or other pertinent mitochondrial metabolic processes. The methods as described herein facilitate rapid, optionally automated, high-throughput screening, with the ability to deposit a cell sample in a well of a multi-well plate, and lyse and analyze the sample in that plate in one, hands-free step.

The present assay includes the steps of determining baseline fluorescence of an ETF in a reaction mixture including lysed cells in a plurality of wells of a multi-well vessel, adding a coenzyme A (CoA) ester substrate for an ACAD of interest to the reaction mixture, and monitoring the change in fluorescence of the ETF thereafter. Those of skill in the art will understand that appropriate blanks and calibration curves can be utilized before, during, and/or after assessment of baseline and post-substrate fluorescence.

The assay described herein is useful for a variety of purposes, including, for example and without limitation, screening individual patients for the presence of an ACAD abnormality or deficiency, and screening compounds and compositions, e.g., prospective active agents, for their activity with respect to ACAD function, for example, for screening small molecule chemical libraries to identify chemicals or drugs for their effect on an ACAD phenotype, or to measure other ACAD activity as a reference control for studying fatty acid β-oxidation or other pertinent mitochondrial metabolic processes. The methods as described herein facilitate rapid, optionally automated, high-throughput screening, with the ability to deposit a cell sample in a well of a multi-well plate, and lyse and analyze the sample in that plate in one, hands-free step.

The assay described herein includes, in certain aspects, only the necessary reactants: the enzyme source (the patient sample), the CoA ester substrate, and the ETF protein. However, those of skill in the art will appreciate that other additions can be made, for example, different buffer protein stabilizers, e.g., glycerol. As used herein, an oxygen scavenger is a composition that removes, decreases, and/or sequesters oxygen to prevent oxygen interaction with assay reagents. In addition, the present assay employs a dual use buffer that both lyses cells and serves as the assay buffer. The present assay also avoids the need for preparing elaborate anaerobic conditions required by earlier assays. Instead, the present assay uses a simple vacuum step and/or scavenging step at the plate level prior to adding the final assay initiator, to remove bubbles and dissolved air. Optionally, some plate readers also can be connected to argon line to flood the bay where the reaction is carried out.

In one aspect, the cell sample comprises white-blood cells of a patient, in which red-blood cells are substantially absent or are not present. According to one aspect, the assay measures MCAD activity in cells, though it will be understood that the assay described herein is suitable for analysis of activity of members of all classes of ACADs. In a non-limiting exemplary method, a white-blood cell preparation is obtained from a patient's blood by any useful method, such as by standard protocols as are broadly known. The sample should be substantially free of red-blood cells or completely free of red-blood cells. As used herein, "substantially free" of blood cells means that any amount of red blood cells present are present in an amount that does not interfere with the assay described herein to any significant degree, and, therefore, are completely or essentially free of red-blood cells. As an example, cells are obtained by a Ficoll-Paque method, with an anticoagulant such as EDTA, as are broadly-known. In other aspects, the cells are obtained from a cell line, which can be useful for drug-screening as described below, such as a lymphoblast cell line.

The cells are placed in a well of a multi-well plate, such as a 96-well plate, with a lysis solution. Solutions for lysing cells are generally known in the art, and, in aspects, include a buffer, glucose, and a detergent. The sample is sonicated in the multi-well plate to aid in lysing the cells, breakup the mitochondrial membrane, and release the ACADs into solution. Sonication can be carried out as broadly known to those of skill in the art.

The methods described herein comprise determining a baseline intrinsic fluorescence of an ETF (a heterodimer of alpha and beta subunits, hereinafter referred to as "ETF"), for example, a porcine ETF, by adding ETF to the reaction mixture (a cellular extract, for example, extracts prepared from white blood cells as described above, leukocytes, lymphoblasts or a cell line thereof), and exposing the ETF to an excitatory wavelength of light at 340-370 nm to determine the reduction of fluorescence of the ETF by monitoring emission at 490-500 nm in the presence of the cellular extract and the substrate.

In one aspect, porcine ETF isolated from pig liver is used in the described assays due to its high fluorescence emission upon excitation. ETF prepared by recombinant technology means using published sequence, may be an alternative, if available. ETF heterodimer amino acid sequences *Sus scrofa* (porcine) and electron transfer flavoprotein subunit beta (ETF-B) (uniProtKB/Swiss-Prot: Q6UAQ8; GenBank Accession Nos. NP_001192208.1 and NM_001205279.1; Entrez Gene, GeneID: 396614) sequences are provided below:

```
GenBank Accession No. AAQ84565 beta subunit
                                                    (SEQ ID NO: 1)
  1 maelralvav krvidfavki rvkpdrtgvv mdgvkhsmnp fceiaveeav rlkekklvke 61 viavscgpaq cqetirtala mgadrgihve vpaaeahhlg plqvarvlak laqkekvdlv 121 llgkqaiddd cnqtgqmtag fldwpqgtfa sqvtlegdkv kvereidggl etlrlklpav 181 vtadlrlnep ryatlpnimk akkkkievik agdlgvdlts klsvvsvedp pqrvagvkve 241 ttedlvaklr eigri
and ETFA (for S. scrofa, UniProtKB: Q6UAQ9):
GenBank Accession No. AAQ84564 alpha subunit
                                                    (SEQ ID NO: 2)
  1 qstiviaeha ndtlapitln titaakrlgg evsclvagtk cdkvaqdlck vagvakvlva 61 qhdaykgllp eeltplvlat qkqfnythic agasafgknl lpriaakldv apisdiiaik 121 spdtfvrpiy agnalctvkc dekvkvfsvr gtsfeaaats ggsaisekas saspvgisew 181 ldqkltksdr peltgakvvv sggrglksge nfkllydlad qlhaavgasr aavdagfvpn 241 dmqvgqtgki vapelyiavg isgaiqhlag mkdsktivai nkdpeapifq vadygivadl 301 fkvvpemtel lkkk
```

Additional ETFs are broadly known and, so long as they fluoresce, e.g., to at least the same level or higher when oxidized (FAD, quinone form), and fluorescence is decreased, e.g., nearly abolished when reduced (FADH, semiquinone form or $FADH_2$, hydroquinone form), they are expected to be useful in the described assays. As an example, while in the recombinant human ETF, Y16L or Y16A fluorescence is multiples that of the recombinant wild type, porcine ETF fluorescence is significantly higher and more stable. Whether a particular ETF or mutant ETF is capable of use in the described methods, e.g., fluoresces, and changes fluorescence under described conditions to a detectable extent, is readily determined by one of ordinary skill.

Once the ETF and the reaction mixture are combined in the wells of the plate or vessel, the wells are deoxygenated. In aspects, deoxygenation is accomplished by covering the wells/plate in such a manner to permit application of vacuum, and a vacuum is applied. Optionally, glucose oxidase/catalase is added to scavenge $O_2$ that may interfere with the reaction, or an oxygen scavenger is utilized in place of vacuum. Alternatively, prior to use all buffers and solution can be purged with argon to remove the available oxygen and kept under argon. The plate is then placed in a plate reader bay, such as described below.

Inside the chamber of the reader, containers with vacuum-degassed CoA ester substrate and ETF solution are placed, for example, with auto inject tubing immersed therein. The reaction mixture and ETF can then be placed under an inert gas environment, meaning that the chamber is flooded with an inert gas, such as argon, to maximize the anaerobic, or substantially free of oxygen, environment either in the liquid reaction mixture or gaseous atmosphere in contact with the liquid. Following the injection of the appropriate amount of ETF, the baseline fluorescence of the reaction mixture is then recorded, for example, over a period of 1 min or longer. While the original published assay specifies excitation at 340 nm and monitoring emission at 492 nm because of instrument limitations, ETF can be excited using a 340 nm filter and monitor its fluorescence using a 490 nm filter. These wavelengths correspond to absorbance and emission peaks of the ETF, but it is noted that other excitation filters/wavelengths, e.g., 355 nm or 370 nm, can be used to obtain higher emission intensity signal, so increase the assay sensitivity.

Once the baseline ETF fluorescence is established, the CoA ester substrate for the ACAD to be analyzed (described below) is added to wells, for example, by injection into the wells with the sample to be assayed. The decrease, or lack of decrease, in ETF fluorescence is monitored over time, for example, in the same manner as the baseline fluorescence after addition of the substrate described above. Monitoring of ETF fluorescence may be initiated immediately after addition of the ACAD substrate. Complete reduction of the ETF flavoprotein dehydrogenase (FAD) flavin moiety by the ACAD:CoA-ester complex nearly eliminates ETF fluorescence at the 492 nm region, and, therefore, a loss of fluorescence at this wavelength is indicative of the presence of the ACAD catalyzing the α,β-dehydrogenation of the added substrate. A control assay, using cells or a cell extract obtained from normal cells or a cell line with known levels of ACADs, can be compared to a test sample, e.g., obtained from a patient, or exposed to an active agent, such as a drug or drug candidate, as described below.

The methods, kits and devices described herein are useful in detecting and quantifying the presence of an ACAD, particularly a human ACAD in a biological sample, such as a cellular extract or a preparation of white blood cells (leukocytes). ACADs catalyze the α,β-dehydrogenation of organic acid CoA esters. Examples of ACADs of significant clinical relevance that can be measured by the assay disclosed herein, and exemplary substrates, include:

Medium-chain specific ($C_4$ to $C_{12}$ straight chain) acyl-Coenzyme A dehydrogenase, encoded by the ACADM gene (e.g., GeneCards® GCID: GC01P075724; HGNC ID: HGNC:89; OMIM 607008; UniProtKB P11310; Entrez Gene Gene, ID: 34), Substrates: $C_6$—CoA to $C_{10}$—CoA, optimum $C_8$—CoA;

Very long chain specific acyl-coenzyme A dehydrogenase, encoded by the ACADVL gene (e.g., GeneCards® GCID: GC17P007218; HGNC ID: HGNC: 92; OMIM 609575; UniProtKB P49748; Entrez Gene, Gene ID: 37), Substrates: $C_{12}$—CoA to $C_{22}$—CoA, optimum $C_{16}$—CoA;

Isovaleryl-coenzyme A dehydrogenase, encoded by the IVD gene (e.g., GeneCards® GCID: GC15P040405; HGNC:6186; OMIM 607036; UniProtKB P26440; Entrez Gene, Gene ID: 3712), Substrates: isovaleryl-CoA, $C_5$—CoA, optimum isovaleryl-CoA;

Short-chain specific acyl-CoA dehydrogenase (SCAD) (ACADS, e.g., GeneCards® GCID: GC12P120761). Substrates: $C_4$—CoA to $C_6$—CoA, optimum $C_4$—CoA;

Long-chain specific acyl-CoA dehydrogenase (LACD) (ACADL, e.g., GeneCards® GCID: GC02M210187). Substrates: $C_{10}$—CoA to $C_{16}$—CoA, 2-methyl-$C_7$—CoA, Chloyl-CoA, optimum $C_{10}$—CoA;

Isobutyryl-CoA dehydrogenase (IBD) (ACAD8, e.g., GeneCards® GCID: GC11P134253). Substrates: isobutyryl-CoA;

Short/branched-chain acyl-CoA dehydrogenase (SB-CAD) (ACADSB, e.g., GeneCards® GCID: GC10P123008). Substrates: 2-methylbutaryl-CoA, $C_4$—CoA, optimum 2-methylbutaryl-CoA;

Acyl-CoA Dehydrogenase Family, Member 9 (ACAD9) (ACAD9, e.g., GeneCards® GCID: GC03P129083). Substrates: $C_{16}$—CoA to $C_{22}$—CoA, optimum $C_{16}$—CoA; and Glutaryl-CoA dehydrogenase (GDH) (GCDH, e.g., GeneCards® GCID: GC19P012891). Substrates: glutaryl-CoA.

As described above, the present assay is performed in a vessel, and preferably in an array of vessels, such as in a well of a multi-well plate, so as to provide a high-throughput assay, allowing rapid testing on multiple samples concurrently. Any commercially-available 4, 6, 8, 12, 16, 24, 48, or 96 well microplate, or any other plate containing a plurality of wells (vessels), for example as available from Thermo Scientific of Rockford Ill., are suitable arrays for purposes herein, so long as they are of sufficient volume to permit performance of the methods described herein and permit fluorescence detection.

The assay described herein includes use of disposable or re-fillable cartridge systems for providing reagents for spectrofluorometric analysis. Plate readers and plate reading technology for such analyses are broadly commercially available for measuring fluorescence of ETF as described herein.

Any method described herein can be automated to any suitable extent by use of robotics and fluidics, and through use of suitable automated systems. Configuration of such systems is within the abilities of those of skill in the art. One non-limiting example of such an automated system is the Digital Microfluidic Platform of Baebies, Inc. of Durham, N.C. Other suitable automated platforms include: FLUOstar Omega, from BMG Labtech, Offenburg, Germany.

In other aspects, the assay as described herein can be used to evaluate drug chaperone candidates binding to stabilize unstable mutants. In such aspects, purified ACAD proteins can be included in the wells in place of the cell free extract together with the candidate drug. In this way, the effect of the drug or therapeutic composition on ACAD activity can be evaluated at different temperatures. As above, a baseline ETF is assessed in the presence of the ACAD of interest and, optionally, in the presence of the drug or composition of interest. Then, also as described above, a substrate for the ACAD is added, with or without a drug or therapeutic composition, and change in fluorescence is measured, to provide an indication of the effect of the drug or composition on ACAD activity.

An exemplary procedure for preparing reagents and for use of the same in identifying and/or quantifying ACDA activity is provided below. Those of skill will understand that the following includes optional steps to account for variations during processing, and that the below can be considered an exemplary standard operating procedure for carrying out the assay described herein.

Preparation of ETF from Pig Liver

Stock solutions are prepared as follows:

PBS for 4 L of 10× stock: 320 g NaCl; 8 g KCl; 57.6 g $Na_2HPO_4$; and 9.6 g $KH_2PO_4$. Dissolve in 3.2 L of $H_2O$. Adjust the pH to 7.4 with HCl or NaOH, and add $H_2O$ to 4 L with $H_2O$.

Homogenization Buffer (HB) (prepares 2 L): 4 ml of 0.5 M EDTA; 50 ml glycerol; 6 ml of 1 M $KH_2PO_4$; 94 ml of 1 M $K_2HPO_4$; and 171.15 g sucrose.

Sonication Buffer (SB) buffer (make 250 ml fresh as needed): 5 ml of 0.5M EDTA; 80 ml of 1M $KPO_4$, pH 8.0; 25 mg FAD; 50 mg AMP; and q.s. with $H_2O$ to 250 ml.

Liver Processing and Isolation of Mitochondria—Day 1

Liver samples are cut into pieces (about 1"×1"), weighed to about 500-600 g, and are washed thoroughly in ice cold PBS or saline to remove blood. Removal of blood can be accomplished by soaking liver tissue pieces in the PBS and gently hand squeezing the pieces to remove blood. Liver pieces are then added to a blender with about the same amount of HB buffer (wt:vol). The tissue is then blended at top speed for about 5 minutes to provide a homogenate. Homogenate is then filtered through two layers of cheesecloth to remove hard connective tissue chunks. The filtered homogenate is then transferred to a container and centrifuged at 3500 RPM (1900 rcf) for 40 minutes.

Supernatant is removed and transferred to separate containers and further centrifuged at 9000 RPM (9700 rcf) for an additional 30 minutes. Supernatant is discarded and pellets combined using HB. HB is then added to the combined pellet and mitochondria are dispersed.

The above steps can be repeated until the final solution of pellet and HB is nearly colorless (pink color nearly abolished). The final pellet is then weighed and stored at −80° C. for at least 3-5 hrs.

Liver Processing and Isolation of Mitochondria—Day 2

Mitochondria Extract Preparation:

More than 200 g×2 of pellet is thawed (either overnight at 4° C. or quickly in a 37° C. water bath. SB is then added to the pellets at 0.3:1 (vol:wt). The pellets in SB are sonicated until the sample becomes homogenous. The homogenous solution is transferred to a glass sonication vessel and sonicated at ~35% power, using a large-volume probe, seven times for 1 min each. The suspension is cooled for 5 min between sonications. The temperature should not be allowed to exceed 10° C., and pH indicator strips are used to ensure that the suspension remains basic. The sample is the centrifuged at 53,000 RPM for 60 minutes, and supernatant is pooled and total volume measured.

Ammonium Sulfate Fractionation

Using a standard ammonium sulfate saturation table, the amount of ammonium sulfate needed to reach 40% saturation at 0° C. is determined, using the following formula:

Amount of ammonium sulfate needed (g)=Vol. of sample (in liters)×grams for 40% saturation into 1 L (obtained from table).

Next, the ammonium sulfate is sprinkled over the sample on ice while stirring, over 30-45 min. The sample is then stirred for 1 hour or more. pH indicator strips are used to ensure that the sample pH is not acidic. Following stirring, the sample is centrifuged at 40,000 RPM in an ultracentrifuge for 30 min. Alternatively, the sample can be centrifuged using a Sorvall centrifuge at 20K rpm for 90 min.

Supernatant is then carefully removed, and supernatant from all tubes is combined and the volume measured to determine the amount of ammonium sulfate needed to reach 60% saturation as shown above. The ammonium sulfate is applied similar to above, and the sample is again centrifuged at 40,000 RPM in an ultracentrifuge for 60 minutes. Supernatant is discarded and the pellets are collected and re-dissolved in a minimal amount of SB.

The dissolved pellets are then dialyzed 3× into 5 L of a 15 mM $K_2HPO_4$ (unbuffered), 5% glycerol solution. Dialyzation should occur for a minimum of 4 hours, with rapid stirring. If it is necessary to dialyze overnight, slow-speed stirring should be used.

Preparation of Anion Exchange Chromatography Resin

Approximately 150 ml of Sepharose-DEAE FF resin suspension is washed well with water to remove storage solution containing ethanol. The resin is then left overnight (or for a few hours before packing) in 100 ml of 1.0 M $K_2HPO_4$ (unbuffered). If needed, the sample can be concentrated with polyethylene glycol powder. Sample size for the DEAE column should preferably be 30 ml or smaller. The dialysis bag is placed in the powder in a cold room at 4° C., on a shaker so that local areas of aggregated or precipitation of proteins are minimized. Injecting a larger volume could cause ETF to fuse with another yellow fluorescent protein that elutes later than ETF from the DEAE step. Concentration can take 2-4 hrs.

Anion Exchange Chromatography—Day 3

Buffered resin (see above) is poured into an XK 50/20 column on a fast protein liquid chromatography (FPLC) machine. The resin is packed and washed with about 0.5 L of 15 mM $K_2HPO_4$ (unbuffered), at 15 ml/min. Column bed height should become ~10-15 cm after packing. Washing is continued until conductivity reading on the FPLC detector is stable reflecting the ionic strength of the buffer.

After packing, the resin is equilibrated in 15 mM $K_2HPO_4$ (unbuffered) in 5% glycerol.

If the sample is too turbid, it can be collected from the dialysis bag and centrifuged at 19,000 rpm (43,000 rcf) for 15 min, or filtered through a crude protein filter (80 µm pore size).

The sample is then transferred to a loading loop, and is injected using a 50-ml sample loop at a flow rate of 2 ml/min. The protein-bound resin is washed with the same buffer as above.

Collection of fractions begins after injection, at 5 ml/fraction. ETF should start to elute between 60-120 ml as a distinct yellow/green peak. If red fractions elute fusing at the tail end of the yellow fractions and/or if another green/yellow peak is fused with the ETF fractions, it may imply sample will not be pure enough. Fractions sometimes become cloudy. If so, monitor the pH and adjust quickly after combining all yellow fractions, to pH 8.3, with a few drops of 1M potassium phosphate monobasic, keeping the sample on ice. If fractions are cloudy, spin at 19,000 RPM (43,000 rcf) in a centrifuge, for example a Sorvall centrifuge, for 30 min.

Cation Exchange Chromatography—Day 3

Sample is injected into CM-Sepharose (carboxymethyl-agarose) resin packed in an XK 16/40 column (bed volume about 75 ml) using an FPLC. The resin is pre-equilibrated with 10 mM Tris pH 8.5. The equilibrating buffer pH eluting from column must be basic. A gradient of buffers is used, with a gradient from 100% Buffer A (10 mM Tris, pH 8.5) to 100% Buffer B (10 mM Tris, 100 mM NaCl, pH 8.5).

Using the FPLC, the protein-bound resin is washed with 100 ml of Buffer A, then eluted with 200 ml gradient from 0% to 100% of Buffer B. ETF should elute as a fluorescent green fraction towards the end of the gradient.

Next, the ratio of $A_{270}/A_{436}$ is determined. Fractions with ratios below 6.5 can be used after concentration and dialysis in storage buffer. Specifically, samples below $A_{270}/A_{436}$ ratio of <6.5 are pooled and concentrated using Amicon concentrators. Fractions with ratios between 6.5 and 10 are pooled and further purified.

Hydroxyapatite Chromatography—Day 4 (Optional if Sample Ratio of $A_{270}/A_{436}$ Below 6.5 is Required, e.g., in Kinetic Studies)

Pooled fractions from the above elution step should be loaded as soon as possible (no dialysis necessary) onto 20 µm ceramic hydroxyapatite, which has been equilibrated in 10 mM potassium phosphate, 5% glycerol, pH 7.6. The column is then developed using Buffer A, $H_2O$, and Buffer B, 0.5 M K phosphate, 5% glycerol, pH 7.6, from 2% to 17% Buffer B in 150 ml total elution volume. Chromatography is run at flow rate of 2.0 ml, fraction volume 5 ml/fraction.

Storage of Samples

Sample buffer is exchanged with 50 mM Tris, pH 8.0 at 4° C., using Amicon concentrators to $Abs_{436\ nm}$ between 1.4 and 2.0. The exchange is kept ice cold to avoid precipitation. The sample is then centrifuged at 14,000 RPM for 15 min. $Abs_{436\ nm}$ is then measured and the concentration determined according to the following formula:

Conc. of ETF=$(A_{436}/13.4)$ mM 1 nmol ETF=[1/(mM of ETF)] µl

Centrifuged sample is then stored at −80° C. after flash freezing without glycerol.

ETF Plate Assay for White Blood Cells or Cultured Lymphoblast:

For lymphoblasts culture, the media used is RPMI medium supplemented with 1% $_L$-glutamine, 1% penicillin streptomycin and 15% fetal bovine serum (FBS) at 37° C., 5% CO2, with humidity. Following incubation to grow cells, cells are counted, and harvested at a 6.7×10$^6$ cells/ml suspension and put in a 15 ml tube. Samples are spun at 200 g for 10 min. Supernatant is then removed. The pellet is resuspended with 8 mL of fresh media. 150 µL is then aliquoted down three columns (24 wells) onto two plates (one control, one compound). If screening for drugs, incubate for 24 hr @ 37° C.

A protein assay is then performed, with 2 µl×3 of sample, using a BioRad DC assay.

1 µl Protease inhibitor is then added, for example Protease Inhibitor Cocktail tablets (Roche Diagnostics GmbH) dissolved in 50 ml. To each well of the plate, 50 µl of lysis solution (200 mM Tris, pH 8.0, 2% glucose, 0.1% Tween 20) is added. Each plate is then sealed with plate sealer.

A plate sonicator is then filled with icy $H_2O$. The plates are sonicated for 20 sec, 30× total, while allowing 10 seconds for cooling off between sonications, 15 min total. Plates are then shaken for 2 min, sonicated for another 10 minutes, and shaken again for 2 minutes.

A vacuum is then applied to the plates for 10 min.

The assay program is then run, in one aspect, the assay program is Microplate Reader (BMG Labtech, Offenburg, Germany). A sample protocol for the assay is as follows:
1. Prime a pump (Pump #1) with 0.3 mM $C_8$—CoA (about 1 ml) and place ice in a beaker.
2. Prime a second pump (Pump #2) with ETF (about 70 μM).
3. Setup plate layout. Set Pump #1 volume (about 5 μl). Set Pump #2 volume (about 10 μl).
4. Save and close software.
5. Add 2 μl glucose oxidase and catalase mix at a ratio of 10:1 (v:v) to each well, and load plate into machine.
6. Run the assay (sample provided below):
   a. Shake 2 seconds.
   b. Blank.
   c. Auto inject ETF before cycle 4.
   d. Shake 2 seconds.
   e. Baseline kinetics.
   f. Auto inject substrate before cycle 64.
   g. Shake 2 seconds.
   h. Read kinetics. End reading after cycle 124.

Each cycle is 1 sec. Phase 1-3 sec. Phase 2-1 min. Phase 3-1 min.

ETF Plate Assay for Patient Samples

Materials

Equipment:
Tissue culture hood and incubator
UV/Vis Spectrophotometer (such as Jasco 6500)
Plate reader, with anaerobic option (such as FLUOstar Omega, from BMG Labtech)
Sonicator with 6 inch cup probe (such as UIP250MTP, from Hielscher)

Supplies:
Flasks—T175
Plates—Microplate 96 well, PS, F-bottom, (chimney well), μClear, TC, Black with lid, sterile (for example from Greiner Bio-One)

Chemicals:
Medium: Roswell Park Memorial Institute (RPMI) medium for lymphoblast culture Substrates: Palmitoyl-CoA ($C_{16}$—CoA), $C_{18}$—CoA, $C_{14}$—CoA, $C_{12}$—CoA, Octanoyl-CoA ($C_8$—CoA) from Sigma
Porcine ETF (see above standard protocol for porcine ETF)
Detergent: Tween-20
Buffer: Tris, phosphate,
Protease inhibitor: Protease Inhibitor Cocktail tablets, for example from Roche Diagnostics GmbH Protocol Wild-type and/or MCADD patients' lymphoblast cells are cultured in RPMI medium supplemented with 1% L-glutamine, 1% penicillin streptomycin and 15% fetal bovine serum (FBS) at 37° C., 5% $CO_2$, and humid incubator. Alternately, lymphocytes are prepared from a patient's blood by standard methods, such as density separation methods, such as Ficoll-Paque methods (such as Ficoll-Paque PLUS from GE Healthcare Life Sciences).

Example 1

Figure 1:
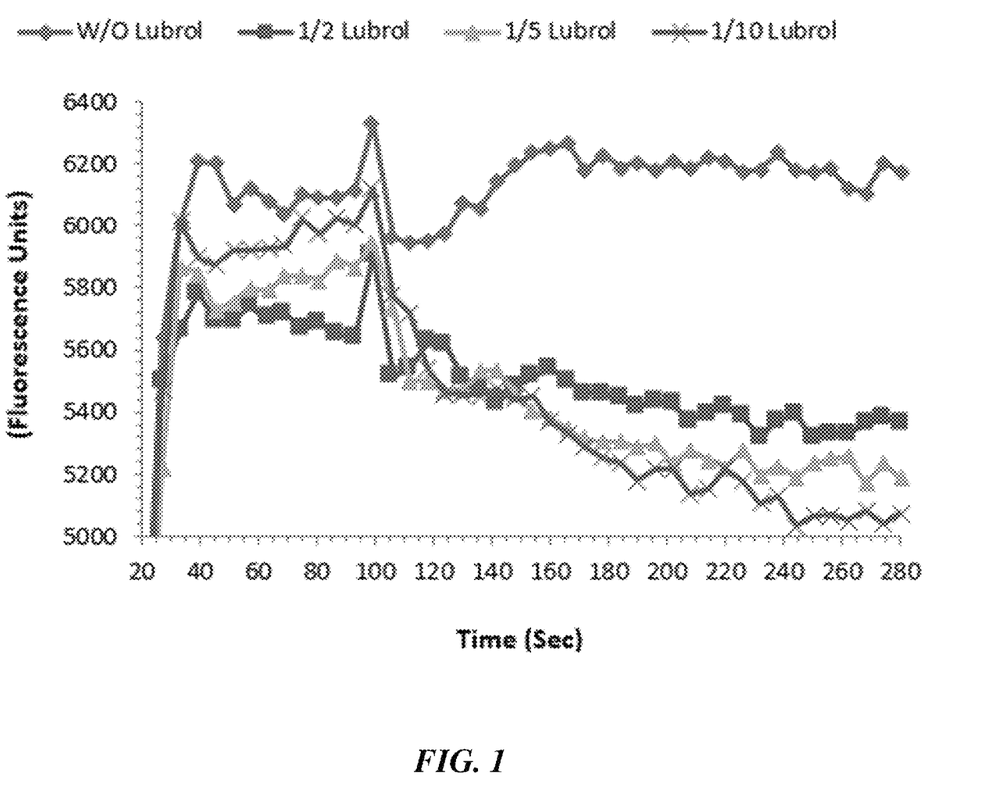
Figure 2:
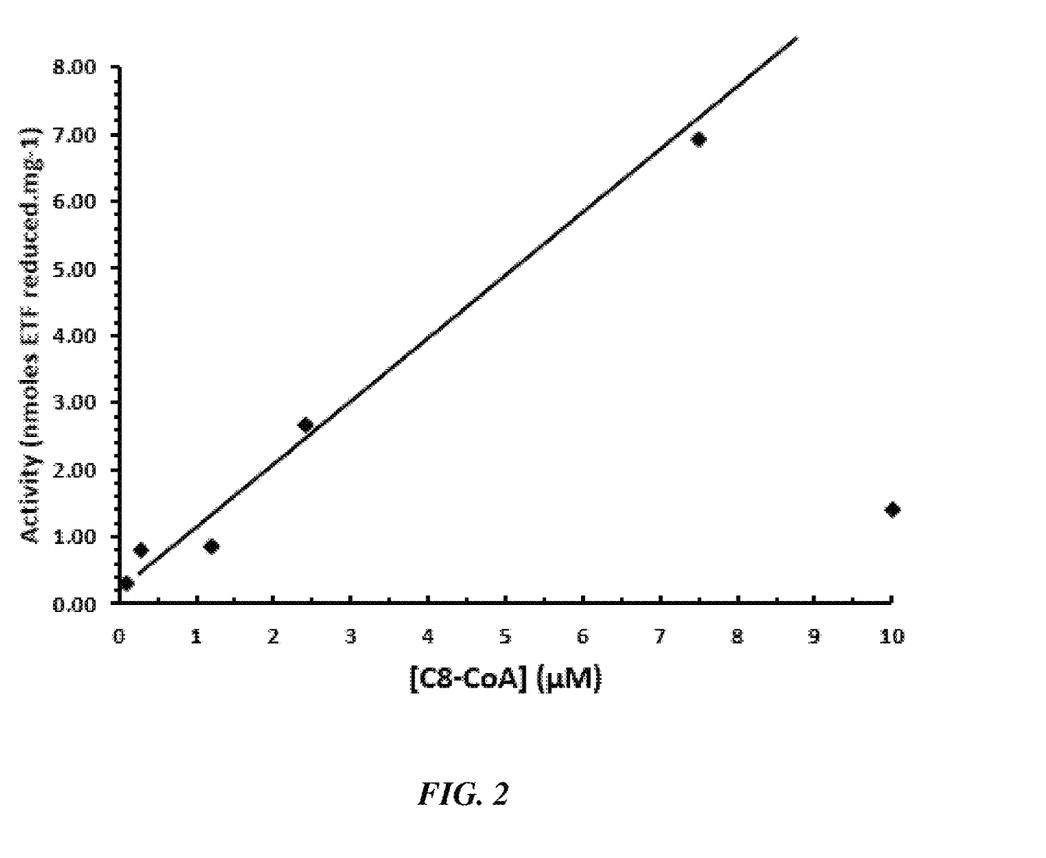
FIG. 2. Optimizing the ETF fluorescence reduction 96-well plate assay at various substrate concentrations. Samples used were TL596 $4 \times 10^5$ cells with lyses done in wells at 0, 0.1, 0.3, 0.6, 7.5, and 10 µM $C_8$—CoA. Reaction was initiated after initial baseline fluorescence monitoring for 100 seconds by addition of $C_8$—CoA to 10 µM. The slope reflecting the drop in fluorescence with time was calculated from 100 seconds up to 140 seconds.

ETF was generated, and assays were conducted, essentially as described above. Results are shown in FIG. 1 and FIG. 2. Results shown in FIG. 1 illustrate the importance of including a detergent to break the cell and mitochondrial membrane and access the enzyme which uses the substrate included in the reaction mixture. After a period of monitoring the baseline fluorescence the decrease in fluorescence was observed to be highest at the lowest concentration of Lubrol (0.1%). Other detergents, including digitonin, that may not damage the enzyme, may also show similar or better performance. FIG. 2 shows increase in activity with increasing substrate concentration, which is consistent with the specificity of the interaction among the reaction components. An excess of up to 30 μM substrate is recommended.

From the innovative standpoint, the method disclosed herein modifies the prior assays, which rely heavily on maintaining anaerobic conditions for the assay. The present method does not require such strict anaerobic conditions, and is manageable with vacuum and including the GO/CAT. The plate reader technology also enables miniaturizing the assay to the micro level.

Clauses: The following numbered clauses provide illustrative and non-limiting examples of various aspects of the invention.

Clause 1: A method of identifying the presence of, or quantifying an Acyl-Coenzyme A Dehydrogenase (ACAD) in a cell sample comprising: a. determining fluorescence of an Electron Transfer Flavoprotein (ETF), in a reaction mixture comprising lysed cells of the cell sample in a well of a multi-well vessel in an anaerobic environment; b. adding a Coenzyme A substrate for the specific ACAD to the reaction mixture; and c. monitoring the change in fluorescence of the ETF at one or more time points after addition of the substrate to the reaction mixture, wherein a loss of fluorescence indicates the presence of an ACAD in the sample.

Clause 2: The method of clause 1, in which the ACAD is human.

Clause 3: The method of clause 1, in which the reaction mixture is vacuum de-gassed and steps a. through c. are conducted under an inert gas, for example, argon.

Clause 4: The method of any one of clauses 1 to 3, in which the ETF is porcine ETF.

Clause 5: The method of any one of clauses 1 to 4, in which the ACAD is a medium-chain specific ($C_4$ to $C_{12}$ straight chain) acyl-Coenzyme A dehydrogenase Clause 6: The method of any one of clauses 1 to 4, in which the ACAD is a very long chain specific ($C_{14}$ to $C_{26}$ straight or branched chain) acyl-CoA dehydrogenase.

Clause 7: The method of any one of clauses 1 to 4, in which the ACAD is an isovaleryl-CoA dehydrogenase.

Clause 8: The method of any one of clauses 1 to 4, in which the ACAD is short-chain specific acyl-CoA dehydrogenase (SCAD); long-chain specific acyl-CoA dehydrogenase (LACD); isobutyryl-CoA dehydrogenase (IBD); short/branched-chain acyl-CoA dehydrogenase (SBCAD); Acyl-CoA Dehydrogenase Family, Member 9 (ACAD9) or glutaryl-CoA dehydrogenase (GDH).

Clause 9: The method of any one of clauses 1 to 8, in which the sample is a cell lysate.

Clause 10: The method of clause 9, in which the cell lysate is a cell lysate of a lymphocyte, lymphoblast, white blood cell or a cell line of any of the preceding.

Clause 11: The method of clause 9, in which the cell lysate is a white blood cell lysate from a patient.

Clause 12: The method of clause 11, in which the white blood cell lysate is obtained from a neonate or a patient less than one year of age.

Clause 13: The method of any one of clauses 1 to 12, in which the sample comprises cells, further comprising preparing the lysed cells by contacting the cell sample in the well with a cell lysis solution comprising a surfactant; and sonicating the sample in the well.

Clause 14: The method of clause 13, wherein the sonicating step comprises sonicating the sample with a sonicator with a cup horn or a microplate horn.

Clause 15: The method of any of clauses 1 to 14, further comprising isolating the ETF.

Clause 16: The method of clause 15, in which the ETF is prepared by a method as described herein.

Clause 17: A multiwell plate comprising a plurality of wells, and at least one well comprising isolated porcine ETF (such that reduction of the ETF, that is of FAD to $FADH_2$, can be detected by loss of fluorescence at 490 nm when excited at 340 nm), a human cell lysate comprising an ACAD, an ACAD substrate (in addition to any present in the cell lysate), and a detergent, and optionally, glucose, glucose oxidase, and catalase.

Clause 18: A method of preparing isolated ETF, comprising: isolating and freezing mitochondria from liver tissue; thawing and sonicating the mitochondria; centrifuging the mitochondrion to produce a supernatant; precipitating the supernatant with ammonium sulfate and centrifuging the sample to produce a pellet; resuspending the pellet in a buffer comprising FAD and adenosine monophosphate; dialyzing the resuspended pellet against a solution of unbuffered $K_2HPO_4$ and glycerol, e.g., 5 to 25 mM $K_2HPO_4$ and from 1 to 10% v/v glycerol; fractionating the dialyzed pellet on an anion exchange material, collecting yellow-green fractions; fractionating the fractions on a cation exchange material, collecting fluorescent green fractions having a ratio of $A_{270}/A_{436}$ of 10 or less; optionally, if the sample has a ratio of $A_{270}/A_{436}$ of from 6.5 to 10 fractionating the fractions on hydroxyapatite; and concentrating the samples.

Clause 19: The method of clause 18, in which the liver is pig liver.

Clause 20: A method of quantifying acyl-coenzyme A dehydrogenase (ACAD) activity in a cell sample comprising: a. determining fluorescence of an electron transfer flavoprotein (ETF) in a reaction mixture comprising lysed cells of the cell sample in a well of a multi-well vessel in an anaerobic environment; b. adding a coenzyme A (CoA) substrate for a specific ACAD to the reaction mixture; and c. monitoring a change in fluorescence of the ETF at one or more time points after addition of the CoA substrate to the reaction mixture, wherein a loss of fluorescence of the ETF indicates the presence of an ACAD in the sample.

Clause 21: The method of clause 20, wherein the cell sample is a human cell sample.

Clause 22: The method of clause 20 or clause 21, wherein the cell sample is substantially free of red blood cells.

Clause 23: The method of clause 20 or clause 21, wherein the cell sample is free of red blood cells.

Clause 24: The method of any of clauses 20-23, wherein oxygen is removed from the reaction mixture in step a. by vacuum or addition of an oxygen scavenger.

Clause 25: The method of any of clauses 20-24, wherein steps a. through c. are conducted under an inert gas environment.

Clause 26: The method of clause 25, wherein the inert gas is argon.

Clause 27: The method of any of clauses 20-26, wherein the ACAD is a medium-chain specific acyl-CoA dehydrogenase, a very long chain specific acyl-CoA dehydrogenase, an isovaleryl-CoA dehydrogenase, a short-chain specific acyl-CoA dehydrogenase, a long-chain specific acyl-CoA dehydrogenase, an isobutyryl-CoA dehydrogenase, a short/branched-chain acyl-CoA dehydrogenase, an Acyl-CoA Dehydrogenase Family, Member 9, or a glutaryl-CoA dehydrogenase.

Clause 28: The method of any of clauses 20-27, wherein the ETF is a porcine ETF.

Clause 29: The method of any of clauses 20-28, wherein the reaction mixture in at least one well further comprises a drug that may affect ACAD activity, and wherein a difference in a change in fluorescence of the ETF in the at least one well in which the drug is present compared to one or more wells in which the drug is not present indicates differences in ACAD activity.

Clause 30: The method of any of clauses 20-29, wherein step b. further comprises adding a drug that may affect ACAD activity to at least one well, and wherein a difference in a change in fluorescence of the ETF in the at least one well in which the drug is present compared to one or more wells in which the drug is not present indicates differences in ACAD activity; and/or the lysed cells in a well are contacted with a drug that may affect ACAD activity prior to lysis, and wherein a difference in a change in fluorescence of the ETF in the at least one well in which the lysed cells were contacted with the drug prior to lysis compared to one or more wells in which the lysed cells were not contacted with the drug prior to lysis indicates differences in ACAD activity.

Clause 31: A method of quantifying acyl-coenzyme A dehydrogenase (ACAD) activity in a cell sample comprising: a. adding the cell sample to a well of a multi-well vessel; b. adding a lysis solution to the well to form a reaction mixture; c. adding an electron transfer flavoprotein (ETF) to the reaction mixture; d. removing oxygen from the reaction mixture; e. determining fluorescence of an electron transfer flavoprotein (ETF) in the reaction mixture; f. adding a coenzyme A (CoA) substrate for a specific ACAD to the reaction mixture; and g. monitoring a change in fluorescence of the ETF at one or more time points after addition of the CoA substrate to the reaction mixture, wherein a loss of fluorescence of the ETF indicates the presence of an ACAD in the sample.

Clause 32: The method of clause 31, wherein the cell sample is substantially free of red blood cells.

Clause 33: The method of clause 31 or clause 32, wherein the reaction mixture is sonicated prior to removing oxygen.

Clause 34: The method of any of clauses 31-33, wherein steps e. through g. are conducted under an inert gas environment.

Clause 35: The method of clause 34, wherein the inert gas is argon.

Clause 36: The method of any of clauses 31-35, wherein oxygen is removed from the reaction mixture by vacuum.

Clause 37: The method of any of clauses 31-36, wherein oxygen is removed from the reaction mixture by addition of an oxygen scavenger. The method of claim 12, wherein the lysis solution comprises a detergent, glucose, and a salt.

Clause 38: The method of any of clauses 31-37, wherein the ACAD is a medium-chain specific acyl-CoA dehydrogenase, a very long chain specific acyl-CoA dehydrogenase, an isovaleryl-CoA dehydrogenase, a short-chain specific acyl-CoA dehydrogenase, a long-chain specific acyl-CoA dehydrogenase, an isobutyryl-CoA dehydrogenase, a short/branched-chain acyl-CoA dehydrogenase, an Acyl-CoA Dehydrogenase Family, Member 9, or a glutaryl-CoA dehydrogenase.

Clause 39: The method of any of clauses 31-38, wherein steps d. through f. are performed using a plate-reading apparatus comprising a processor and a non-transitory, computer readable medium containing programming instructions that, when executed by the processor, cause steps d. through f. to be performed automatically.

Clause 40: The method of any of clauses 31-39, wherein the ETF is a porcine ETF.

Clause 41: The method of any of clauses 31-40, wherein a drug that affects ACAD activity is added to at least one well containing the reaction mixture in one of steps a., b., or c, and wherein a difference in a change in fluorescence of the ETF in the at least one well in which the drug is present compared to one or more wells in which the drug is not present indicates differences in ACAD activity.

Clause 42: The method of any of clauses 31-40 wherein a drug that affects ACAD activity is added to at least one well containing the reaction mixture in step f, and wherein a difference in a change in fluorescence of the ETF in the at least one well in which the drug is present compared to one or more wells in which the drug is not present indicates differences in ACAD activity.

Clause 43: A method of quantifying acyl-coenzyme A dehydrogenase (ACAD) activity in a cell sample comprising: a. adding the cell sample, comprising at least one ACAD, to a plurality of wells of a multi-well vessel; b. adding a lysis solution to the plurality of wells to form a reaction mixture; c. adding an electron transfer flavoprotein (ETF) to the reaction mixture; d. adding a drug that may affect ACAD activity to at least one, but not all, of the plurality of wells containing the reaction mixture; e. removing oxygen from the reaction mixture; f. determining fluorescence of an electron transfer flavoprotein (ETF) in the reaction mixture; g. adding a coenzyme A (CoA) substrate for the ACAD to the reaction mixture to initiate reaction; and h. monitoring a change in fluorescence of the ETF at one or more time points after addition of the CoA substrate to the reaction mixture, wherein a difference in a change in fluorescence of the ETF in the at least one well in which the drug is present compared to one or more wells in which the drug is not present indicates differences in ACAD activity.

Clause 44: The method of clause 43, wherein the cell sample is a human cell sample.

Clause 45: The method of clause 42 or clause 43, wherein the cell sample is derived from a lymphoblast or lymphocyte cell line.

Clause 46: The method of any of clauses 43-45, wherein the cell sample is substantially free of red blood cells.

Clause 47: The method of any of clauses 43-45, wherein the cell sample is free of red blood cells.

Clause 48: The method of any of clauses 43-47, wherein the ETF is a porcine ETF.

Clause 49: The method of any of clauses 43-48, wherein the ACAD is a medium-chain specific acyl-CoA dehydrogenase, a very long chain specific acyl-CoA dehydrogenase, an isovaleryl-CoA dehydrogenase, a short-chain specific acyl-CoA dehydrogenase, a long-chain specific acyl-CoA dehydrogenase, an isobutyryl-CoA dehydrogenase, a short/branched-chain acyl-CoA dehydrogenase, an Acyl-CoA Dehydrogenase Family, Member 9, or a glutaryl-CoA dehydrogenase.

Clause 50: The method of any of clauses 43-49, wherein the lysis solution comprises a detergent, glucose, and a salt.

Clause 51: The method of any of clauses 43-50, wherein oxygen is removed from the reaction mixture by vacuum.

Clause 52: The method of any of clauses 43-51, wherein oxygen is removed from the reaction mixture by addition of an oxygen scavenger.

The present invention has been described in accordance with the above standard procedures and example, which are intended to be illustrative in all aspects rather than restrictive. Thus, the present invention is capable of many variations in detailed implementation, which may be derived from the description contained herein by a person of ordinary skill in the art.

We claim:

1. A method of quantifying acyl-coenzyme A dehydrogenase (ACAD) activity in a cell sample comprising:
   a. measuring a baseline fluorescence of an electron transfer flavoprotein (ETF) in a reaction mixture comprising lysed cells of the cell sample in an open-to-air well of a multi-well vessel by exposing the ETF to light of an excitatory wavelength and measuring fluorescence at an emission wavelength;
   b. adding a coenzyme A (CoA) substrate for a specific ACAD to the reaction mixture; and
   c. monitoring a change in fluorescence of the ETF at one or more time points after addition of the CoA substrate to the reaction mixture by comparing the baseline fluorescence of the ETF to the fluorescence of the ETF at the one or more time points after addition of the CoA substrate to the reaction mixture,
   wherein a loss of fluorescence of the ETF indicates the presence of an ACAD in the sample, and
   wherein the reaction mixture of step a is subjected to deaeration prior to measuring the baseline fluorescence, and wherein measuring the baseline fluorescence, adding a CoA substrate, and monitoring the change in fluorescence are carried out in an air-containing environment.

2. The method of claim 1, wherein the cell sample is a human cell sample.

3. The method of claim 2, wherein the cell sample is free of red blood cells.

4. The method of claim 1, wherein air is removed from the reaction mixture by vacuum.

5. The method of claim 1, wherein the ACAD is a medium-chain specific acyl-CoA dehydrogenase, a very long chain specific acyl-CoA dehydrogenase, an isovaleryl-CoA dehydrogenase, a short-chain specific acyl-CoA dehydrogenase, a long-chain specific acyl-CoA dehydrogenase, an isobutyryl-CoA dehydrogenase, a short/branched-chain acyl-CoA dehydrogenase, an Acyl-CoA Dehydrogenase Family, or Member 9 (ACAD9).

6. The method of claim 1, wherein the ETF is a porcine ETF from a native or recombinant source.

7. The method of claim 1, wherein the reaction mixture in at least one well further comprises a drug that affects ACAD activity, and wherein a difference in a change in fluorescence of the ETF in the at least one well in which the drug is present compared to one or more wells in which the drug is not present indicates differences in ACAD activity.

8. The method of claim 1, wherein:
   step b. further comprises adding a drug that may affect ACAD activity to at least one well, and wherein a difference in a change in fluorescence of the ETF in the at least one well in which the drug is present compared to one or more wells in which the drug is not present indicates differences in ACAD activity; and/or
   the lysed cells in a well are contacted with a drug that affects ACAD activity prior to lysis, and wherein a difference in a change in fluorescence of the ETF in the at least one well in which the lysed cells were contacted with the drug prior to lysis compared to one or more wells in which the lysed cells were not contacted with the drug prior to lysis indicates differences in ACAD activity.

9. A method of quantifying acyl-coenzyme A dehydrogenase (ACAD) activity in a cell sample comprising:
   a. adding the cell sample to a well of a multi-well vessel;
   b. adding a lysis solution to the well to form a reaction mixture and subjecting the reaction mixture to a deaeration process;
   c. adding an electron transfer flavoprotein (ETF) to the reaction mixture;
   d. exposing the reaction mixture to an air-containing environment;
   e. measuring baseline fluorescence of an electron transfer flavoprotein (ETF) in the reaction mixture by exposing the ETF to light of an excitatory wavelength and measuring fluorescence at an emission wavelength;
   f. adding a coenzyme A (CoA) substrate for a specific ACAD to the reaction mixture; and
   g. monitoring a change in fluorescence of the ETF at one or more time points after addition of the CoA substrate to the reaction mixture by comparing the baseline fluorescence of the ETF to the fluorescence of the ETF at the one or more time points after addition of the CoA substrate to the reaction mixture,
   wherein a loss of fluorescence of the ETF indicates the presence of an ACAD in the sample.

10. The method of claim 9, wherein the cell sample is free of red blood cells.

11. The method of claim 9, wherein air is removed from the reaction mixture by vacuum.

12. The method of claim 9, wherein the lysis solution comprises a detergent, glucose, and a salt.

13. The method of claim 9, wherein the ACAD is a medium-chain specific acyl-CoA dehydrogenase, a very long chain specific acyl-CoA dehydrogenase, an isovaleryl-CoA dehydrogenase, a short-chain specific acyl-CoA dehydrogenase, a long-chain specific acyl-CoA dehydrogenase, an isobutyryl-CoA dehydrogenase, a short/branched-chain acyl-CoA dehydrogenase, an Acyl-CoA Dehydrogenase Family, or Member 9 (ACAD9).

14. The method of claim 9, wherein the ETF is a porcine ETF.

15. The method of claim 9, wherein a drug that affects ACAD activity is added to at least one well containing the reaction mixture in one of steps a., b., or c., and wherein a difference in a change in fluorescence of the ETF in the at least one well in which the drug is present compared to one or more wells in which the drug is not present indicates differences in ACAD activity.

16. The method of claim 9, wherein a drug that affects ACAD activity is added to at least one well containing the reaction mixture in step f., and wherein a difference in a change in fluorescence of the ETF in the at least one well in which the drug is present compared to one or more wells in which the drug is not present indicates differences in ACAD activity.

17. A method of quantifying acyl-coenzyme A dehydrogenase (ACAD) activity in a cell sample comprising:
   a. adding the cell sample, comprising at least one ACAD, to a plurality of wells of a multi-well vessel;
   b. adding a lysis solution to the plurality of wells to form a reaction mixture and subjecting the reaction mixture to a deaeration process;
   c. adding an electron transfer flavoprotein (ETF) to the reaction mixture;
   d. adding a drug that may affect ACAD activity to at least one, but not all, of the plurality of wells containing the reaction mixture;
   e. exposing the reaction mixture to an air-containing environment;
   f. measuring baseline fluorescence of an electron transfer flavoprotein (ETF) in the reaction mixture by exposing the ETF to light of an excitatory wavelength and measuring fluorescence at an emission wavelength;
   g. adding a coenzyme A (CoA) substrate for the ACAD to the reaction mixture to initiate reaction; and
   h. monitoring a change in fluorescence of the ETF at one or more time points after addition of the CoA substrate to the reaction mixture by comparing the baseline fluorescence of the ETF to the fluorescence of the ETF at the one or more time points after addition of the CoA substrate to the reaction mixture, wherein a difference in a change in fluorescence of the ETF in the at least one well in which the drug is present compared to one or more wells in which the drug is not present indicates differences in ACAD activity.

18. The method of claim 17, wherein the cell sample is derived from a lymphoblast or lymphocyte cell line.

* * * * *